US012806199B2

United States Patent
(12) United States Patent
Karp et al.

(10) Patent No.: US 12,806,199 B2
(45) Date of Patent: Nov. 24, 2026

(54) TREATMENT OF INFECTIONS IN AND AROUND THE EYE

(71) Applicant: UNIVERSITY OF MIAMI, Miami, FL (US)

(72) Inventors: Carol Karp, Miami, FL (US); Anat Galor, Miami, FL (US)

(73) Assignee: University of Miami, Miami, FL (US)

( * ) Notice: Subject to any disclaimer, the term of this patent is extended or adjusted under 35 U.S.C. 154(b) by 488 days.

(21) Appl. No.: 18/562,100

(22) PCT Filed: May 18, 2022

(86) PCT No.: PCT/US2022/029842
§ 371 (c)(1),
(2) Date: Nov. 17, 2023

(87) PCT Pub. No.: WO2022/245950
PCT Pub. Date: Nov. 24, 2022

(65) Prior Publication Data

US 2024/0238292 A1 Jul. 18, 2024

Related U.S. Application Data

(60) Provisional application No. 63/190,454, filed on May 19, 2021.

(51) Int. Cl.

| | |
|---|---|
| ***A61P 27/02*** | (2006.01) |
| ***A61K 9/00*** | (2006.01) |
| ***A61K 31/513*** | (2006.01) |
| ***A61K 45/06*** | (2006.01) |
| ***A61P 33/14*** | (2006.01) |

(52) U.S. Cl.
CPC .......... *A61K 31/513* (2013.01); *A61K 9/0048* (2013.01); *A61K 45/06* (2013.01); *A61P 27/02* (2018.01); *A61P 33/14* (2018.01)

(58) Field of Classification Search
CPC .... A61K 31/513; A61K 9/0048; A61K 45/06; A61P 27/02; A61P 33/14
See application file for complete search history.

(56) References Cited

U.S. PATENT DOCUMENTS

| | | | | |
|---|---|---|---|---|
| 2003/0211163 A1* | 11/2003 | Chong | A61K 45/06 514/45 |
| 2014/0323995 A1 | 10/2014 | Clauson et al. | |
| 2015/0238601 A1 | 8/2015 | Boxer et al. | |

FOREIGN PATENT DOCUMENTS

| | | | |
|---|---|---|---|
| WO | 2011075415 A1 | 6/2011 | |
| WO | 2015/105905 A1 | 7/2015 | |
| WO | WO 2015/105905 * | 7/2015 | A61K 35/26 |
| WO | 2016/134130 A1 | 8/2016 | |

OTHER PUBLICATIONS

International Search Report and Written Opinion received in PCT/US2022/029842 mailed Jul. 29, 2022, Apr. 27, 2026.

Rodrigues et al., Topical Drug Delivery to the Posterior Segment of the Eye: Addressing the Challenge of Preclinical to Clinical Translation, Pharmaceutical Research, vol. 35, No. 245, 29, Oct. 2018, pp. 1-5.

Ho et al., Role of Topical 5-Fluorouracil in Demodex-Associated Blepharitis, The American Ophthalmological Society, May 21, 2021, p. 19, [Jul. 7, 2022], Retrieved from Internet: <URL: https://www.aosOnline.org/assets/Annual-Meeting/Program-Books/A0S21-Program-Book-FINAL-REV,pdf> •.

Rufli T, Mumcuoglu Y. The Hair Follicle Mites Demodex folliculorum and Demodex brevis: Biology and Medical Importance. Dermatology. 1981;162(1):1-11. doi:10.1159/000250228.

Cheng AMS, Sheha H, Tseng SCG. Recent advances on ocular Demodex infestation. Curr Opin Ophthalmol. 2015;26 (4):295-300. doi: 10.1097/ICU.0000000000000168.

Liu J, Sheha H, Tseng SC. Pathogenic role of Demodex mites in blepharitis. Curr Opin Allergy Clin Immunol. 2010;10 (5):505-510. doi:10.1097/ACI.0b013e32833df9f4.

Luo X, Li J, Chen C, Tseng S, Liang L. Ocular Demodicosis as a Potential Cause of Ocular Surface Inflammation. Cornea. 2017;36:S9-S14. doi: 10.1097/ICO.0000000000001361.

Liang L, Ding X, Tseng SCG. High Prevalence of Demodex brevis Infestation in Chalazia. Am J Ophthalmol. 2014;157 (2):342-348. e1. doi:10.1016/j.ajo.2013.09.031.

Kemal M, Sümer Z, Toker MI, Erdoğan H, Topalkara A, Akbulut M. The Prevalence of Demodex folliculorum in Blepharitis Patients and the Normal Population. Ophthalmic Epidemiol. 2005; 12(4):287-290. doi:10.1080/092865805910057.

Wolf R, Ophir J, Avigad J, Lengy J, Krakowski A. The hair follicle mites (*Demodex* spp.). Could they be vectors of pathogenic microorganisms? Acta Derm Venereol. 1988;68(6) 535-537. http://www.ncbi.nlm.nih.gov/pubmed/2467494.

Zhang AC, Muntz A, Wang MTM, Craig JP, Downie LE. Ocular Demodex _: a systematic review of the clinical literature. Ophthalmic Physiol Opt. 2020;40(4):389-432. doi:10.1111/opo.12691.

Vargas-Arzola J, Segura-Salvador A, Torres-Aguilar H, et al. Prevalence and risk factors to Demodex folliculorum infection in eyelash follicles from a university population of Mexico. Acta Microbiol Immunol Hung. Mar. 2020:1-5. doi:10.1556/030.2020.01067.

Kabataş N, Doğan AŞ, Kabataş EU, Acar M, Biçer T, Gürdal C. The Effect of Demodex Infestation on Blepharitis and the Ocular Symptoms. Eye Contact Lens Sci Clin Pract. 2017;43(1):64-67. doi:10.1097/ICL.0000000000000234.

Erbagci Z, Erbagci I, Erkilic S. High incidence of demodicidosis in eyelid basal cell carcinomas. Int J Dermatol. 2003;42 (7):567-571. doi:10.1046/j.1365-4362.2003.01928.x.

Yamashita LSF de F, Cariello AJ, Geha NMA, Yu MCZ, Hofling-Lima AL. Demodex folliculorum on the eyelash follicle of diabetic patients. Arq Bras Oftalmol. 2011;74(6):422-424. doi:10.1590/S0004-27492011000600008.

(Continued)

*Primary Examiner* — Erich A Leeser
(74) *Attorney, Agent, or Firm* — Meunier Carlin & Curfman LLC

(57) ABSTRACT

Disclosed herein are methods for the treatment of *Demodex* including the step of contacting the *Demodex* with 5-fluorouracil, or salt thereof. Disclosed herein are ophthalmic compositions including 5-fluorouracil or salt thereof suitable for the treatment of *Demodex*.

17 Claims, No Drawings

(56) References Cited

OTHER PUBLICATIONS

Wiwanitkit S, Wiwanitkit V. Prevalence of eyelash demodex among human immunodeficiency virus infected patients at different CD4+ count status. Int J Trichology. 2013;5(3):166. doi:10.4103/0974-7753.125625.

Keles H, Pancar Yuksel E, Aydin F, Senturk N. Pre-Treatment and Post-Treatment Demodex Densities in Patients under Immunosuppressive Treatments. Medicina (B Aires). 2020;56(3): 107. doi:10.3390/medicina56030107.

Jansen T, Kastner U, Kreuter A, Altmeyer P. Rosacea-like demodicidosis associated with acquired immunodeficiency syndrome. Br J Dermatol. 2001; 144(1):139-142. doi:10.1046/j.1365-2133.2001.03794.x.

Ivy SP, Mackall CL, Gore L, Gress RE, Hartley AH. Demodicidosis in childhood acute lymphoblastic leukemia: An opportunistic infection occurring with immunosuppression. J Pediatr. 1995; 127(5):751-754. doi:10.1016/S0022-3476(95)70168-0.

Tighe S, Gao Y-Y, Tseng SCG. Terpinen-4-ol is the Most Active Ingredient of Tea Tree Oil to Kill Demodex Mites. Transl Vis Sci Technol. 2013;2(7). doi:10.1167/tvst.2.7.2.

Gao Y-Y. In vitro and in vivo killing of ocular Demodex by tea tree oil. Br J Ophthalmol. 2005;89(11). doi:10.1136/bjo.2005.072363.

Koo H, Kim TH, Kim KW, Wee SW, Chun YS, Kim JC. Ocular Surface Discomfort and Demodex_: Effect of Tea Tree Oil Eyelid Scrub in Demodex Blepharitis. J Korean Med Sci. 2012;27(12):1574. doi:10.3346/jkms.2012.27.12.1574.

Karakurt Y, Zeytun E. Evaluation of the Efficacy of Tea Tree Oil On the Density of Demodex Mites (Acari: Demodicidae) and Ocular Symptoms In Patients With Demodectic Blepharitis. J Parasitol. 2018;104(5):473-478. doi:10.1645/18-46.

Al Bayyat G, Arreaza-Kaufman D, Venkateswaran N, Galor A, Karp CL. Update on pharmacotherapy for ocular surface squamous neoplasia. Eye Vis. 2019;6(1):24. doi:10.1186/s40662-019-0150-5.

Theotoka D, Morkin MI, Galor A, Karp CL. Update on Diagnosis and Management of Conjunctival Papilloma. Eye Vis. 2019;6(1):18. doi:10.1186/s40662-019-0142-5.

Ávila MY, Martínez-Pulgarín DF, Rizo Madrid C. Topical ivermectin-metronidazole gel therapy in the treatment of blepharitis caused by *Demodex* spp.: A randomized clinical trial. Contact Lens Anterior Eye. May 2020. doi:10.1016/j.clae.2020.04.011.

Savla K, Le JT, Pucker AD. Tea tree oil for Demodex blepharitis. Cochrane Database Syst Rev. Jun. 2020. doi:10.1002/14651858.CD013333.pub2.

Ghiringhelli F, Bruchard M, Apetoh L. Immune effects of 5-fluorouracil: Ambivalence matters. Oncoimmunology. 2013;2(3):2-3. doi:10.4161/onci.23139.

Dingsdag SA, Hunter N. Metronidazole: an update on metabolism, structure-cytotoxicity and resistance mechanisms. J Antimicrob Chemother. 2018;73(2):265-279. doi:10.1093/jac/dkx351.

Extended European Search Report for European Application No. 22805404.5, dated Jan. 31, 2025, 11 Pages.

Joag M.G., et al., "Topical 5-Fluorouracil 1% as Primary Treatment for Ocular Surface Squamous Neoplasia," Ophthalmology, 2016, vol. 123, No. 7, pp. 1442-1448 (7 pages), DOI: 10.1016/J.OPHTHA.2016.02.034.

* cited by examiner

TREATMENT OF INFECTIONS IN AND AROUND THE EYE

CROSS-REFERENCE TO RELATED APPLICATION

This application is a U.S. National Stage application filed under 35 U.S.C. § 371 of PCT/US2022/029842, filed on May 18, 2022, which claims the benefit of priority to U.S. Provisional Application No. 63/190,454, filed on May 19, 2021, the contents of which are hereby incorporated herein by reference in their entirety.

FIELD OF THE INVENTION

The invention is directed to compositions and methods for the treatment of infections and infestations. In some embodiments, the invention is directed to compositions and methods for the treatment of *Demodex* infestations and infections secondary thereto.

BACKGROUND

*Demodex* are obligatory parasites that can be found within and around hair follicles in humans, including within the eye lashes. Two distinct species of *Demodex* mites have been identified in humans: *Demodex folliculorum* and *Demodex brevis*. The main food source for the two species is sebum. It is thought that mites also feed on follicular and glandular epithelial cells, leading to direct damage of the lid margin. *Demodex* infestation of the skin, eyelids and lashes has been associated with anterior blepharitis, meibomian gland dysfunction, chalazia formation, and keratoconjunctivitis.

The exact mechanism of action behind the pathogenic role of *Demodex* in blepharitis remains unclear. One hypothesis is that *Demodex* act as a nidus producing bacterial superantigens which stimulate the immune system. Another hypothesis is that *Demodex*, especially *folliculorum*, mechanically irritates the epithelium of the hair follicles, inducing epithelial hyperplasia and reactive hyperkeratinization. *Demodex brevis* is thought to burrow deep into the meibomian glands and its chitinous exoskeleton may cause deeper granulomatous reactions which result in chalazia formation. Various ophthalmic risk factors for ocular *Demodex* presence include ocular rosacea, recurrent pterygia, and contact lens wear. Systemic factors associated with ocular *Demodex* include obesity, smoking, malignancy, chemotherapeutic agents, diabetes mellitus, and acquired immunodeficiency syndrome. A shared feature of these risk factors is their association with impaired immunity.

The management of ocular democidosis is difficult and requires long-term treatment. Thus far, nothing is curative. Tea tree oil is the most common component of eyelid cleansing products marketed to treat *Demodex* blepharitis. Studies have shown that the active ingredient in tea tree oil, terpinene-4-ol, kills *Demodex folliculorum* in a dose dependent fashion. Several clinical trials have shown significant reduction in *Demodex* count with tea tree oil. However, patients in these studies were generally healthy with relatively low numbers of *Demodex* at baseline. Oral and topical anti-parasitic agents are another therapeutic strategy, especially in refractory cases. Studies showing potential efficacy include the use of permethrin cream, oral ivermectin, and combination oral ivermectin and metronidazole. Despite these treatment options, *Demodex* infestation remains difficult to eradicate.

There remains a need for improved methods and compositions for treating infestations and infections of the eye and surrounding areas. There remains a need for improved methods and compositions for treating bacterial, fungal, and parasitic infestations and infections. There remains a need for improved methods and compositions for treating *Demodex*. There remains a need for improved methods and compositions for treating infections associated with *Demodex*.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As used herein, "*Demodex*" refers to a genus of ectoparasitic mites within the Arachnida class that live in or near hair follicles of mammals. *Demodex folliculorum* and *Demodex brevis* are the two main species commonly found on humans.

As used herein, "aracidal" agents are compounds (or mixtures of compounds) that kill or otherwise arrest or inhibiting the growth or development of parasitic organisms.

"Miticidal" agents are compounds (or mixtures of compounds) that kill or otherwise arrest the growth or development of mites.

Arrest or inhibiting the growth or development of parasitic organisms refers to the inhibition of the progression from one stage in a parasite's (or mite's) life cycle to a more mature stage. For example, the transition between various larval forms or transition from larvae to proto-nymph or from proto-nymph to nymph, or from nymph to adult. Aracidal and miticidal agents includes those which damage and/or destroy eggs, larvae, and/or adult forms of the target organism.

Compounds disclosed herein may be provided in the form of pharmaceutically acceptable salts. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate.

Disclosed herein are methods of treating *Demodex* in a subject in need thereof by contacting the *Demodex* with 5-fluorouracil or a salt thereof. In certain embodiment, the method includes administering a composition including 5-fluorouracil ("5-FU"), salt or prodrug thereof, to the subject. In certain embodiments, the *Demodex* is located on or around one or more sites of the eye, for instead on the eyelid, eyelid margin, eyelash, eyelash follicles, eyebrow, eyebrow follicles, cornea, or corner of the eye. In some embodiments, the composition is topically applied to the subject. For example, the composition may be applied directly to the *Demodex* (i.e., applied to skin/hair directly harboring the *Demodex*). In other embodiments, the composition can be indirectly applied to *Demodex*. Combinations of physical forces (e.g., gravity, wicking) and physiological processes deliver the composition from the site of application to the *Demodex*. In certain embodiments, the composition is topically applied, both directly and indirectly, to the *Demodex*. In some embodiments, the composition is administered to the skin around the eye or one or more portions of the lacrimal apparatus, for example, eyelash, eyelid, eye surface, eyebrow, orbit, extraocular muscles, conjunctiva, canthus, caruncle or combination thereof.

Also disclosed herein are methods and compositions for treating infections in subjects also infested with *Demodex*. Exemplary infections include bacterial infections, fungal infections, as well as infestation with other parasitic organisms.

Since *Demodex* mites can carry bacterial reservoirs, and may also carry other infective organisms, *Demodex* infestation can lead to infection with such organisms. Such infections caused by *Demodex* are designated herein as "infections secondary to *Demodex*." Disclosed herein are compositions and methods for treating infections secondary to *Demodex*. Exemplary infections include bacterial infections, fungal infections, as well as infestation with other parasitic organisms.

In some instances, the subject experiencing *Demodex* infestation will also experience an infection which is not directly caused by an organism introduced by a *Demodex* vector. Such an infection is designated herein as a contemporaneous infection. Thus, also disclosed herein are methods of treating infections secondary to *Demodex*. In further embodiments, disclosed herein are method of treating infections that are contemporaneous, but not secondary, to *Demodex*. Exemplary infections include bacterial infections, fungal infections, as well as infestation with other parasitic organisms.

The composition may be applied to the intended location using a variety of implements. For example, the composition can be applied using a dropper, swab, cosmetic pad, wipe, wipe stick, towelette, sponge, gauze, puff, wand, brush, or comb.

In further embodiments, the composition is applied by means other than topical, e.g., oral or parenteral administration. Such non-topical administrations may be combined with topical administration.

In certain embodiments, the *Demodex* includes *Demodex brevis* and/or *Demodex folliculorum*, or a combination thereof. For example, the *Demodex* can include both *Demodex brevis* and *Demodex folliculorum*, while in other embodiments the *Demodex* does not include a *Demodex brevis* component, and in yet other embodiments the *Demodex* does not include a *Demodex folliculorum* component. The compositions and methods disclosed herein be used to treat fungal infections secondary to *Demodex*, bacterial infections secondary *Demodex*, and combinations thereof. The compositions and methods disclosed herein be used to treat fungal infections contemporaneous to *Demodex*, bacterial infections contemporaneous to *Demodex*, and combinations thereof. Exemplary infections that can be treated include acanthamoeba, bacterial keratitis, yeast, parasitic infections, and the like.

The compositions and methods disclosed herein can be used to treat a variety of conditions associated with *Demodex*. For example, in some embodiments the compositions and methods can be used to treat a patient experiencing ocular demodicosis, anterior and/or posterior blepharitis, meibomian gland dysfunction, chalazia formation, keratoconjunctivitis, keratitis, or a combination thereof.

In some embodiments, the subject can be diagnosed with *Demodex* prior to commencing treatment. In some instances, the diagnosis can be made by visual inspection of the eye and surrounding area, especially the eyelash. In some instances the diagnosis can include the step of epilating one or more eyelashes from a subject, and then visually inspecting the epilated eyelash for the presence of *Demodex*. In some instances the visual inspection can be made using magnification. After one or more applications of the therapeutic composition, the subject may be reevaluated for *Demodex*, and if need, additional course of treatment applied.

The compositions disclosed herein may be administered using a variety of different treatment regimes. For example, the subject may receive the composition once or several times over a period of 1-100 days, 50-100 days, 1-75 days, 25-75 days, 1-50 days, 21-50 days, 1-28 days, 14-28 days, 1-21 days, 7-21 days, 1-14 days, 3-14 days, 5-14 days, 5-10 days, 7-10 days, 6-8 days, or 7 days. Over such a period of time, the subject may receive the composition once a day, twice a day, three times a day, four times a day, or more than four times a day. In other instances, the patient may receive the composition once every two days, once every three days, and the like. In certain embodiments, the composition is administered to the subject once every 24 hours, once every 12 hours, once every 10 hours, once every 8 hours, once every 6 hours, once every 4 hours, once every 2 hours, once every 1 hour, or once every 30 minutes per day.

In some embodiments, the composition may be administered using a cyclic regimen, for instance with a first segment in which the composition is administered (according to the dosing regimens defined above), followed by a second segment in which the composition is not administered. The second segment may have a duration of 1-100 days, 25-100 days, 50-100 days, 1-75 days, 50-75 days, 25-75 days, 1-60 days, 5-60 days, 7-60 days, 14-60 days, 21-60 days, 28-60 days, 7-56 days, 14-56 days, 21-56 days, 28-56 days, 7-49 days, 14-49 days, 21-49 days, 28-49 days, 7-42 days, 14-42 days, 21-42 days, 28-42 days, 7-35 days, 14-35 days, 21-35 days, 7-28 days, 14-28 days, 7-21 days, 14-21 days, 7-14 days, 7 days, 14-21 days, 14-28 days, 14-35 days, 14-42 days 14-49 days, 14 days, 21-49 days, 21-42 days, 21-35 days, 21-28 days, 21 days, or 28 days.

The subject may receive one or more cycles of treatment (defined herein a one segment where the composition is administered and one segment where the composition is not administered). In some embodiments, the subject may receive at least 2, at least 3, at least 4, at least 5, or at least 6 cycles of treatment. In other embodiments, the subject may receive from 1-10 cycles, from 5-10 cycles, from 1-8 cycles, from 4-8 cycles, from 1-6 cycles, from 3-6 cycles, from 1-5 cycles, from 2-4 cycles, from 1-4 cycles, from 1-3 cycles, from 1-2 cycles, 2 cycles, 3 cycles, 4 cycles, or 5 cycles of treatment.

The therapeutic compositions suitable for use in the disclosed methods may include 5-fluorouracil in an amount effective to kill or otherwise arrest the growth or development of *Demodex*. In certain embodiments, the composition can include 5-fluorouracil in an amount from 0.1-10.0 wt %, from 0.1-0.5 wt %, from 0.25-0.75 wt %, from 0.5-1.0 wt %, from 0.75-1.25 wt %, from 0.5-1.5 wt %, from 1.0-2.5 wt %, from 1.0-5.0 wt %, from 2-4 wt %, from 3-5 wt %, from 2.5-7.5 wt %, from 4.0-6.0 wt %, from 5.0-7.5 wt %, from 5.0-10.0 wt %, or from 7.5-10.0 wt %.

Compositions suitable for use in the disclosed methods can be formulated as a solution or liquid dispersion, and will include water as a carrier. In some embodiments, the compositions can include water in an amount from 25.0-99.9 wt %, from 50.0-99.9 wt %, from 75.0-99.9 wt %, from 95.0-99.9 wt %, from 80.0-99.0 wt %, from 85.0-99.0 wt %, 90.0-98.0 wt %, from 85-95 wt %, from 75.0-90.0 wt %, from 65.0-80.0 wt %, from 55.0-70 wt %, from 45.0-60.0 wt %, from 35.0-50.0 wt %, or from 25.0-45.0 wt %.

The compositions may be formulated at a pH suitable for administration to one or more locations on or around the eye, and may be formulated to increase the availability of the 5-fluorouracil to the parasitic organism. In certain embodiments, the composition has a pH from 4.0-8.0, from 5.0-8.0, from 6.0-8.0, from 6.0-7.5, from 6.0-7.0, from 6.0-6.5, from 6.5-7.0, from 6.5-7.5, from 6.5-8.0, from 7.0-7.5, from 7.0-8.0, from 7.5-8.0, from 7.1-7.5, from 7.2-7.5, or from 7.3-7.5.

The compositions may be formulated with a tonicity suitable for administration to one or more locations on or around the eye, for example, the composition can be isotonic to lacrimal fluid. In other embodiments, the composition can be hypertonic to lacrimal fluid. The composition can have an osmolarity from 250-500 mOsm/L, from 250-450 mOsm/L, from 250-400 mOsm/L, from 250-350 mOsm/L, from 250-325 mOsm/L, from 280-325 mOsm/L, or from 300-325 mOsm/L.

The compositions may be formulated at a viscosity suitable for administration to one or more locations on or around the eye. Viscosity may be measured at 23 °C, at a shear rate of 1 Hz. Suitable viscosities for the compositions include 1-10,000 cps, 1-5,000 cps, 2,500-10,000 cps, 2,500-7,500 cps, 5,000-10,000 cps, 1-100 cps, 25-250 cps, 25-100 cps, 50-150 cps, 50-250 cps, 100-500 cps, 250-750 cps, 500-1,000 cps, 500-1,500 cps, 1,000-2,000 cps, 1,500-2,500 cps, 2,000-3,000 cps, 2,500-3,500 cps, 3,000-4,000 cps, 3,500-4,500 cps, 4,000-5,000 cps, 4,500-5,500 cps, 5,000-6,000 cps, 5,500-6,500 cps, 6,000-7,000 cps, 6,500-7,500 cps, 7,000-8,000 cps, 7,500-8,500 cps, or 9,000-10,000 cps.

The composition may be formulated as an ointment. Exemplary ointments will include a pharmaceutically acceptable base, for example liquid petrolatum, white petrolatum, plastibase, hard paraffin, white soft paraffin, yellow soft paraffin, liquid paraffin, emulsifying wax, microcrystalline wax, white bees wax, yellow bees wax, carnauba wax, wool wax (wool fat), mineral oil, olive oil, purified lanolin, anhydrous lanolin, polyethylene glycol (e.g., polyethylene glycol 400 or polyethylene glycol 3350), propylene glycol, polyoxyethylene, polyoxypropylene, and combinations thereof. In other embodiments, the composition does not include a base, as defined herein.

The composition may be formulated as emulsion having an oil phase, which can include one or more emulsifiers, emollients, or combination thereof. Suitable emulsions can include an oil phase in an amount from 15-75 wt %, from 15-50 wt %, from 15-30 wt %, from 20-40 wt %, from 25-50 wt %, from 30-60 wt %, or from 45-75 wt %. The composition can include an emulsifier in an amount from 1-20 wt %, from 1-10 wt %, from 5-15 wt %, or from 10-20 wt %.

In certain embodiments, the compositions disclosed can include vegetable oil, mineral oil, animal oil, synthetic oil, silicone oils, isopropyl palmitate, 1-decene polymer (hydrogenated), $C_{12}$-$C_{15}$ alkyl benzoate, $C_{12}$-$C_{15}$ alkyl benzoates esters, lanolin alcohol, isopropyl myristate, or a combination thereof.

In certain embodiments, the disclosed compositions can include a surfactant, for example an ionic surfactant, nonionic surfactant, or a combination thereof. Exemplary surfactants include cetostearyl alcohol, cetyl alcohol, cocamide DEA, cocamide MEA, isoceteth-20, oleyl alcohol, sorbitan monostearate, sorbitan tristearate, stearyl alcohol, tyloxapol, softigen, solutol HS15, poloxamers (e.g., Pluronic F-68LF™, Lutrol F68, Pluronic L-62LF™, Pluronic L62D™ polysorbates (e.g., polysorbate 20 and polysorbate 80), polyoxyethylene fatty acid esters (e.g., Emulphor) and combination thereof. In other embodiments, the composition does not include a surfactant.

In certain embodiments, the disclosed compositions can include a gelling agent. In some embodiments, the composition can include gum, agar, carrageenan, petrolatum, carboxymethylcellulose, hydroxyethyl cellulose, hydroxymethyl cellulose, sodium hyaluronate, or a combination thereof. In other embodiments, the composition does not include a gelling agent.

Suitable excipients for the formulation can include petrolatum, mineral oil, sodium hyaluronate, propylparaben, methylparaben, polysorbate, dimethicone, cyclomethicone, lanolin, chlorobutanol, water, lanolin alcohol, sodium thiosulfate, sodium phosphate monobasic, phenylmercuric acetate, mannitol, zinc chloride, sodium phosphate, potassium acetate, hypromelloses, gentamcicin sulfate, boric acid, sodium hydroxide, carboxymethylcellulose, polycarbophil, sodium alginate, lanolin oil, carbomer homopolymer type b (allyl pentaerythritol crosslinked), or benzalkonium chloride. However, in some embodiments, the composition does not include a paraben.

In certain embodiments, the disclosed compositions can include a preservative. Exemplary preservatives include chlorine dioxide, benzalkonium chloride, benzethonium chloride, cetrimide, dequalinium chloride, cetylpyridinium chloride, phenylmercuric nitrate, phenylmercuric acetate, thimerosal, chlorobutanol, phenylethyl alcohol, benzyl alcohol, esters of parahydroxybenzoic acid, chlorhexidine, chlorocresol, benzoic acid, polymyxin, ocularly acceptable salts thereof, or a combination thereof. In other embodiments, the composition does not include a preservative.

In certain embodiments, the disclosed compositions can include an antioxidant, for example butylated hydroxytoluene, ascorbic acid, ascorbic palmitate, butylated hydroxyanisole, 2,4,5-trihydroxybutyrophenone, 4-hydroxymethyl-2,6-di-tert-butyl phenol, erythorbic acid, gum guaiac, propyl gallate, thiodipropionic acid, dilauryl thiodipropionate, tert-butylhydroquinone, tocopherol, sodium metabisulfite, sodium sulfite, or a combination thereof. The antioxidant may be present in the compositions in an amount from 0.01-1.0 wt %, from 0.01-0.75 wt %, from 0.01-0.5 wt %, from 0.01-0.25 wt %, from 0.01-0.1 wt %, from 0.05-0.15 wt %, from 0.1-1.0 wt %, from 0.1-0.5 wt %, from 0.1-0.25 wt %, from 0.25-1.0 wt %, from 0.5-1.0 wt %, or from 0.25-0.75 wt %. In other embodiments, the composition does not include an antioxidant.

In certain embodiments, the disclosed compositions can include a humectant, for example the composition can include propylene glycol, glycerin, polyethylene glycol, or a combination thereof. In other embodiments, the composition does not include a humectant.

In certain embodiments, a mild abrasive may be co-administered with the 5-fluorouracil, to facilitate penetration of the active agent(s) into the *Demodex*. In some embodiments, the abrasive includes particles having an average particle size from 1-1,000 microns, from 500-1,000 microns, from 250-750 microns, from 250-500 microns, from 100-500 microns, from 100-250 microns, from 50-200 microns, from 50-150 microns, from 25-100 microns, from 10-100 microns, from 10-50 microns, or from 10-25 microns. Suitable materials for the abrasive include aluminum oxide, barium sulfate, boron nitride, calcium carbonate, cellulose acetate, ceramic, diamond, diatomaceous earth, emerald, ethylene/acric acid copolymer, fibers, garnet, glass, kaolin, lauroyl lysine, lava, magnesium oxide, mica, modified starch, nylon, other metals, other polymers, other silicon dioxides or silicon containing materials, polyethylene, polymethyl methacrylate polypropylene, polystyrene, polytetrafluoroethylene (PTFE), pumice, ruby, sand, sapphire, seashells, sericite, silica, silicon dioxide, silicon carbide, sodium bicarbonate, sodium chloride crystals, starch, silk, talc, topaz, zeolite, polymer particles, or a combination thereof.

In other embodiments, the 5-fluorouracil is not co-administered with an abrasive.

In some embodiments, the 5-fluorouracil is administered as part of a multi-drug regimen to treat *Demodex*. In some embodiments, the method includes administering an additional aracidal, antimicrobial agent, anti-inflammatory agent, as well as combinations thereof. In certain instances, the one or more additional agents is included to treat any accompanying infection (whether secondary or contemporaneous to the *Demodex*).

Suitable aracidal agents that may be co-administered with the 5-fluorouracil include ivermectin, permethrin, niclosamide, tea tree oil, benzoyl peroxide, tapinarof, metronidazole, tea tree oil, and combinations thereof.

In some embodiments the 5-fluorouracil can be co-administered with an antibiotic. In alternative embodiments, the *Demodex* is treated without administering an antibiotic to the patient. As used herein, "antibiotic" is intended to mean an active agent different than 5-fluorouracil, which in some embodiments itself has antibiotic activity.

In some embodiments the 5-fluorouracil can be co-administered with an anti-inflammatory agent. Exemplary anti-inflammatories that can be co-administered with 5-fluorouracil include glucocorticoid, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, 2-arylpropionic acids, N-arylanthranilic acids, oxicams, coxibs, or sulphonanilides, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-beta, interferon-gamma, interleukin-2, antihistamine, antileukotriene, beta-agonists, theophylline, or anticholinergic, antibiotics, tacrolimus, retinoid, or combination thereof.

In some embodiments the 5-fluorouracil can be co-administered with boric acid.

In some embodiments the 5-fluorouracil can be co-administered with a steroid. Exemplary steroids include clobetasol, betamethasone, diflorasone, fluocinonide, flurandrenolide, halobetasole, amcinonide, desoximetasone, halcinonide, fluticasone, triamcinolone, fluocinolone, hydrocortisone, dexamethasone, difluprednate, fluoromethalone, loteprednol etabonate, rimexolone mometasone, triamcinolone, alclometasone, denoside, prednicarbate, or a combination thereof.

In some embodiments the 5-fluorouracil can be co-administered with a non-steroidal anti-inflammatory drug ("NSAID"). Exemplary non-steroidal anti-inflammatory drugs include alminoprofen, benoxaprofen, carprofen, dexibuprofen, dexketoprofen, fenbufen, fenoprofen, flunoxaprofen, flurbiprofen, ibuprofen, ibuproxam, indoprofen, ketoprofen, loxoprofen, pirprofen, suprofen, tiaprofenic acid, ketorolac, alclofenac, bromfenac, diclofenac, etodolac, aceclofenac, sulindac, oxaprozin, faislamine, ethenzamide, diflunisal, benorilate, nabumetone, tolmetinor, salicylamide, salicyl salicylate, methyl salicylate, magnesium salicylate, choline magnesium salicylate, amoxiprin, acetyl salicylic acid, acemetacin, indometacin, oxametacin, proglumetacin, droxicam, lomoxicam, meloxicam, piroxicam, tenoxicam, lornoxicam, tenoxicam, or a combination thereof.

In other embodiments, the 5-fluorouracil is not co-administered with an additional active agent. In other embodiments, the 5-fluorouracil is not co-administered with an additional aracidal agent.

For embodiments in which the 5-fluorouracil is administered in combination with one or more other active agents, the various agents may be administered in separate compositions, or may be administered as a single composition containing two or more active agents. Thus, the disclosure in part relates to a pharmaceutical compositions and kits including 5-fluorouracil for the treatment of *Demodex*, wherein the compositions and kits further include one or more additional agents or abrasive.

In certain embodiments, the 5-fluorouracil composition contains ivermectin, permethrin, niclosamide, tea tree oil, benzoyl peroxide, tapinarof metronidazole, tea tree oil, and combinations thereof.

In certain embodiments, the 5-fluorouracil composition contains an antibiotic. In alternative embodiments, the 5-fluorouracil composition does not contain an antibiotic.

In certain embodiments, the 5-fluorouracil composition contains an anti-inflammatory agent. Exemplary anti-inflammatories include prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, 2-arylpropionic acids, N-arylanthranilic acids, oxicams, coxibs, or sulphonanilides, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-beta, interferon-gamma, interleukin-2, antihistamine, antileukotriene, beta-agonists, theophylline, or anticholinergic, antibiotics, tacrolimus, retinoid, or combination thereof.

In certain embodiments, the 5-fluorouracil composition contains boric acid.

In certain embodiments, the 5-fluorouracil composition contains a steroid. Exemplary steroids include clobetasol, betamethasone, diflorasone, fluocinonide, flurandrenolide, halobetasole, amcinonide, desoximetasone, halcinonide, fluticasone, triamcinolone, fluocinolone, hydrocortisone, dexamethasone, difluprednate, fluoromethalone, loteprednol etabonate, rimexolone mometasone, triamcinolone, alclometasone, denoside, prednicarbate, or a combination thereof.

In certain embodiments, the 5-fluorouracil composition contains a non-steroidal anti-inflammatory drug ("NSAID"). Exemplary non-steroidal anti-inflammatory drugs include alminoprofen, benoxaprofen, carprofen, dexibuprofen, dexketoprofen, fenbufen, fenoprofen, flunoxaprofen, flurbiprofen, ibuprofen, ibuproxam, indoprofen, ketoprofen, loxoprofen, pirprofen, suprofen, tiaprofenic acid, ketorolac, alclofenac, bromfenac, diclofenac, etodolac, aceclofenac, sulindac, oxaprozin, faislamine, ethenzamide, diflunisal, benorilate, nabumetone, tolmetinor, salicylamide, salicyl salicylate, methyl salicylate, magnesium salicylate, choline magnesium salicylate, amoxiprin, acetyl salicylic acid, acemetacin, indometacin, oxametacin, proglumetacin, droxicam, lomoxicam, meloxicam, piroxicam, tenoxicam, lornoxicam, tenoxicam, or a combination thereof.

In certain embodiments, the 5-fluorouracil composition contains a mild abrasive. In some embodiments, the abrasive includes particles having an average particle size from 1-1,000 microns, from 500-1,000 microns, from 250-750 microns, from 250-500 microns, from 100-500 microns, from 100-250 microns, from 50-200 microns, from 50-150 microns, from 25-100 microns, from 10-100 microns, from 10-50 microns, or from 10-25 microns. Suitable materials for the abrasive include aluminum oxide, barium sulfate, boron nitride, calcium carbonate, cellulose acetate, ceramic, diamond, diatomaceous earth, emerald, ethylene/acric acid copolymer, fibers, garnet, glass, kaolin, lauroyl lysine, lava, magnesium oxide, mica, modified starch, nylon, other metals, other polymers, other silicon dioxides or silicon containing materials, polyethylene, polymethyl methacrylate polypropylene, polystyrene, polytetrafluoroethylene (PTFE), pumice, ruby, sand, sapphire, seashells, sericite, silica, silicon dioxide, silicon carbide, sodium bicarbonate, sodium chloride crystals, starch, silk, talc, topaz, zeolite, polymer particles, or a combination thereof. In other embodiments, the composition does not include an abrasive.

Further disclosed herein are kits for the treatment of *Demodex*, wherein the kit includes a first composition containing 5-fluorouracil as defined herein, and at least one additional, separate, composition containing one or more additional active agents or abrasive.

In certain embodiments, the kit includes a separate composition containing ivermectin, permethrin, niclosamide, tea tree oil, benzoyl peroxide, tapinarof metronidazole, tea tree oil, and combinations thereof.

In certain embodiments, the kit includes a separate composition containing an antibiotic.

In certain embodiments, the kit includes a separate composition containing an anti-inflammatory agent. Exemplary anti-inflammatories that can be co-administered with 5-fluorouracil include glucocorticoid, prednisone, cortisone acetate, prednisolone, methylprednisolone, dexamethasone, betamethasone, triamcinolone, beclometasone, fludrocortisone acetate, deoxycorticosterone acetate, aldosterone, salicylates, arylalkanoic acids, 2-arylpropionic acids, N-arylanthranilic acids, oxicams, coxibs, or sulphonanilides, valdecoxib, celecoxib, rofecoxib, leflunomide, gold thioglucose, gold thiomalate, aurofin, sulfasalazine, hydroxychloroquinine, minocycline, infliximab, etanercept, adalimumab, abatacept, anakinra, interferon-beta, interferon-gamma, interleukin-2, antihistamine, antileukotriene, beta-agonists, theophylline, or anticholinergic, antibiotics, tacrolimus, retinoid, or combination thereof.

In certain embodiments, the kit includes a separate composition containing boric acid.

In certain embodiments, the kit includes a separate composition containing a steroid. Exemplary steroids include clobetasol, betamethasone, diflorasone, fluocinonide, flurandrenolide, halobetasole, amcinonide, desoximetasone, halcinonide, fluticasone, triamcinolone, fluocinolone, hydrocortisone, dexamethasone, difluprednate, fluoromethalone, loteprednol etabonate, rimexolone mometasone, triamcinolone, alclometasone, denoside, prednicarbate, or a combination thereof.

In certain embodiments, the kit includes a separate composition containing a non-steroidal anti-inflammatory drug ("NSAID"). Exemplary non-steroidal anti-inflammatory drugs include alminoprofen, benoxaprofen, carprofen, dexibuprofen, dexketoprofen, fenbufen, fenoprofen, flunoxaprofen, flurbiprofen, ibuprofen, ibuproxam, indoprofen, ketoprofen, loxoprofen, pirprofen, suprofen, tiaprofenic acid, ketorolac, alclofenac, bromfenac, diclofenac, etodolac, aceclofenac, sulindac, oxaprozin, faislamine, ethenzamide, diflunisal, benorilate, nabumetone, tolmetinor, salicylamide, salicyl salicylate, methyl salicylate, magnesium salicylate, choline magnesium salicylate, amoxiprin, acetyl salicylic acid, acemetacin, indometacin, oxametacin, proglumetacin, droxicam, lomoxicam, meloxicam, piroxicam, tenoxicam, lomoxicam, tenoxicam, or a combination thereof.

In certain embodiments, the kit includes a separate composition containing a mild abrasive. In some embodiments, the abrasive includes particles having an average particle size from 1-1,000 microns, from 500-1,000 microns, from 250-750 microns, from 250-500 microns, from 100-500 microns, from 100-250 microns, from 50-200 microns, from 50-150 microns, from 25-100 microns, from 10-100 microns, from 10-50 microns, or from 10-25 microns. Suitable materials for the abrasive include aluminum oxide, barium sulfate, boron nitride, calcium carbonate, cellulose acetate, ceramic, diamond, diatomaceous earth, emerald, ethylene/acric acid copolymer, fibers, garnet, glass, kaolin, lauroyl lysine, lava, magnesium oxide, mica, modified starch, nylon, other metals, other polymers, other silicon dioxides or silicon containing materials, polyethylene, polymethyl methacrylate polypropylene, polystyrene, polytetrafluoroethylene (PTFE), pumice, ruby, sand, sapphire, seashells, sericite, silica, silicon dioxide, silicon carbide, sodium bicarbonate, sodium chloride crystals, starch, silk, talc, topaz, zeolite, polymer particles, or a combination thereof.

EXAMPLES

The following examples are for the purpose of illustration of the invention only and are not intended to limit the scope of the present invention in any manner whatsoever.

Example 1: Ex Vivo Treatment of *Demodex* with 5-Fluorouracil

Epilated lashes from an individual with confirmed *Demodex* infection were mounted onto six slides and covered with a coverslip. The lashes were then immersed in 1-2 drops of treatment solution (50 mg/mL 5-FU, 5 mg/mL 5-FU, or balanced salt solution as a control (2 slides each)). The slides were examined under a microscope (at magnifications ranging from 20-40×) every four hours. The kill time was defined as the elapsed time between the addition of test solution and all cessation of movement of the body, legs, mouth and pedipalps for a minimum of 60 seconds. The kill time for *Demodex*-infested lashes immersed in 5 mg/mL of 5-FU, 50 mg/mL of 5-FU, and control were 32 hours, 44 hours, and 72 hours, respectively.

Example 2: Clinical Treatment of *Demodex* with 5-Fluorouracil

Eleven individuals with the clinical diagnosis of demodicosis were identified. The diagnosis of ocular demodicosis was based on clinical examination and confirmed by lash sampling and identification of microscopic mites. Lashes with cylindrical dandruff (CD), (scales that form clear cuffs collaring the lash root) were specifically selected for epilation. External slit lamp photos of both eyes of each individual were taken prior to and after initiation of 5-FU treatment. The majority of individuals were white (n=7) males (n=10); 4 self-identified as Hispanic. The average age of the population was 67±15 years (range 30-83 years). 11 eyes from 10 individuals were diagnosed with OSSN and 1 eye (1 individual) with papilloma. All 22 eyes had clinically significant *Demodex* blepharitis as defined by the presence CDs, with *Demodex* mites subsequently identified in epilated lashes.

Patients were treated with 5-FU in a cyclical fashion (one week of topical 5-FU 1% application 4 times per day in the affected eye(s) followed by a 3-week holiday comprised one cycle). All individuals were treated with at least 2 cycles of 5-FU (mean 4±2 cycles). Treated eyes had a reduction in collarettes and lid inflammation by clinical examination as compared to untreated eye. In the one individual who received bilateral 5-FU treatment, both eyes showed a reduction in CDs and inflammation as compared to pre-treatment.

Example 3: Clinical Treatment of *Demodex* with Mitomycin

A 66-year-old female patient with conjunctival melanoma and heavy *Demodex* infestation underwent topical mitomycin C treatment experienced a dramatic reduction in lash collarettes after 2 cycles.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term “comprising” and variations thereof as used herein is used synonymously with the term “including” and variations thereof and are open, non-limiting terms. Although the terms “comprising” and “including” have been used herein to describe various embodiments, the terms “consisting essentially of” and “consisting of” can be used in place of “comprising” and “including” to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

The invention claimed is:

1. A method of treating an infection or infestation in a subject in need thereof, comprising contacting one or more sites on or around one or both eyes, ocular adnexa, or combination thereof, of the subject with a composition comprising 5-fluorouracil, or salt thereof;

wherein the patient is experiencing ocular demodicosis.

2. The method according to claim 1, wherein the infection or infestation comprises *Demodex.*

3. The method according to claim 1, wherein the patient is experiencing anterior and/or posterior blepharitis, meibomian gland dysfunction, chalazia formation, keratoconjunctivitis, keratitis, or a combination thereof.

4. The method according to claim 1, comprising diagnosing the subject with *Demodex* infection or infestation by epilation, visual analysis of the eyelash, or combination thereof, followed by administration of the composition to the subject.

5. The method according to claim 1, wherein the composition is administered as a cycle of treatment, wherein each cycle of treatment comprises a first segment wherein the composition is administered to the subject, followed by second segment wherein the composition is not administered to the subject, wherein the first segment has a duration of 1-14 days, the second segment has a duration of 1-60 days, and the subject receives at least 2 cycles of treatment.

6. The method according to claim 1, wherein the composition comprises 5-fluorouracil in an amount from 0.1-10.0 wt %.

7. The method according to claim 1, wherein the composition has an osmolarity from 250-500 mOsm/L.

8. The method according to claim 1, wherein the composition has a viscosity from 1-10,000 cps, measured at 23 °C, at a shear rate of 1 Hz.

9. The method according to claim 1, wherein the composition is an ointment comprising a pharmaceutically acceptable base.

10. The method according to claim 1, wherein the composition is an emulsion comprising an oil phase comprising an emulsifier, an emollient, or a combination thereof.

11. The method according to claim 10, wherein the composition comprises an emulsifier comprising an ionic surfactant, non-ionic surfactant, or a combination thereof.

12. The method according to claim 1, wherein the composition comprises a gelling agent.

13. The method according to claim 1, wherein the composition comprises propylene glycol, glycerin, polyethylene glycol, or a combination thereof.

14. The method according to claim 1, wherein the composition comprises an additional aracidal, antimicrobial agent, anti-inflammatory agent, or combination thereof.

15. The method according to claim 1, wherein the composition comprises a steroid.

16. The method according to claim 1, wherein the composition comprises an abrasive.

17. The method according to claim 1, wherein the composition does not include an additional active agent.

* * * * *